United States Patent [19]

Burch

[11] Patent Number: 5,135,917

[45] Date of Patent: Aug. 4, 1992

[54] INTERLEUKIN RECEPTOR EXPRESSION INHIBITING ANTISENSE OLIGONUCLEOTIDES

[75] Inventor: Ronald M. Burch, Silver Spring, Md.

[73] Assignee: Nova Pharmaceutical Corporation, Baltimore, Md.

[21] Appl. No.: 551,977

[22] Filed: Jul. 12, 1990

[51] Int. Cl.$^5$ .................. A61K 31/70; C07H 21/00
[52] U.S. Cl. .............................. 514/44; 536/27; 536/28; 536/29; 530/351
[58] Field of Search ............... 536/27, 28, 29; 514/44

[56] References Cited

U.S. PATENT DOCUMENTS 4,689,320  8/1987  Akira ............................ 514/44
5,075,222 12/1991  Hannum et al. ............... 435/69.1

OTHER PUBLICATIONS

Sims, J. E. et al., cDNA Expression Cloning of the Il-1 Receptor a Member of the Immunoglobulin Superfamily, Sci. 241:585–590 (1988).

Sims J. E. et al., Cloning the Interleukin 1 Receptor From Human T Cells, Proc. Natl. Acad. Sci. USA 86:8946–8950 (1989).

Sumikawa K. and R. Miledi, Receptor of Nicotinic Acetylcholin Receptor Expressions by Antisense RNA and an Oligonucleotide, Proc. Natl. Acad. Sci. USA 85:1302–1306 (1988).

Zheng. H. et al., Specific Inhibition of Cell-Surface T-Cell Receptor Expression by Antisense Oligodeoxynucleotides and its Effect on the Production of an Antigen-specific Regulator T-Cell Factor, Proc. Natl. Acad. Sci. as USA 86:3758–3762 (1989).

Chua, A. O. and Gubler, U., Sequence of the cDNA For The Human Fibroblast Type Interleukin-1 Receptor, Nucleic Acid Res. 17:10114 (1989).

Cohen, J. S., Designing Antisense Oligonucleotides as Pharmaceutical Agents, Trends in Pharmacol. Sci.: 10(11)435–437 (1989).

Stec. W. J. et al., Automated Solid-Phase Synthesis, Separation, and Stereochemistry of Phosphorothioate Analogues of Oilgodeoxyribonucleotides, J. Am. Chem. Soc. 106:6077–6079 (1984).

Adams, S. P. et al., Hindered Dialkylamino Nucleoside Phosphate Reagents in the Synthesis of Two DNA 51-MERS, J. Am. Chem. Soc. 105:661–663 (1983).

Agarwal, K. L. and Riftina, F., Synthesis and Enzymatic Properties of Deoxyribooligonucleotides Containing Methyl and Phenylphosphonate Linkages, Nucl. Acids Res. 6(9):3009–3024 (1979).

Synthesis 1(1) 1988, published by Synthecell Corp., Gaithersburg, Md.

Marcus-Sekura, C. J. Techniques for Using Antisense Oligodeoxyribonucleotides to Study Gene Expression, Anal. Biochem. 172:289–295 (1988).

Weintraub, H. M., Antisense RNA and DNA, Sci. AM. pp. 40–46 (1990).

Van Der Krol, A. R., et al., Modulation of Eukaryotic Gene Expression by Complimentary RNA or DNA Sequences, BioTechniques 6(10):958–976 (1988).

*Primary Examiner*—John W. Rollins
*Assistant Examiner*—L. Eric Crane
*Attorney, Agent, or Firm*—Vincent L. Fabiano

[57] ABSTRACT

Disclosed are oligonucleotide compounds that inhibit interleukin receptor expression when administered to a human subject. Also disclosed are pharmaceutical compositions and methods for inhibiting human interleukin receptor expression.

10 Claims, 2 Drawing Sheets

FIGURE 1

CCTCCTGAGAAGCTGGACCCCTTGGTAAAACACAAGGCCTTCTCCAAGAAGAATATGAAAGTGTTACTC
AGACTTATTTGTTTCATAGCTCTACTGATTTCTTCT    1

CTGGAGGCTGATAAATGCAAGGAACGTGAAGAAAAAATAATTTTAGTGTCATCTGCAAATGAAATTGAT
GTTCGTCCCTGTCCTCTTAACCCAAATGAA___CAC    102

AAAGGCACTATAACTTGGTATAAAGATGACAGCAAGACACCTGTATCTACAGAACAAGCCTCCAGGATT
CATCAACACAAAGAGAAACTTTGGTTTGTTCCTGCT    207

AAGGTGGAGGATTCAGGACATTACTATTGCGTGGTAAGAAATTCATCTTACTGCCTCAGAATTAAAATA
AGTGCAAAATTTGTGGAGAATGAGCCTAACTTATGT    312

TATAATGCACAAGCCATATTTAAGCAGAAACTACCCGTTGCAGGAGACGGAGGACTTGTGTGCCCTTAT
ATGGAGTTTTTTAAAAATGAAAATAATGAGTTACCT    417

AAATTACAGTGGTATAAGGATTGCAAACCTCTACTTCTTGACAATATACACTTTAGTGGAGTCAAAGAT
AGGCTCATCGTGATGAATGTGGCTGAAAAGCATAGA    522

GGGAACTATACTTGTCATGCATCCTACACATACTTGGGCAAGCAATATCCTATTACCCGGGTAATAGAA
TTTATTACTCTAGAGGAAAACAAACCCACAAGGCCT    627

GTGATTGTGAGCCCAGCTAATGAGACAATGGAAGTAGACTTGGGATCCCAGATACAATTGATCTGTAAT
GTCACCGGCCAGTTGAGTGACATTGCTTACTGGAAG    732

TGGAATGGGTCAGTAATTGATGAAGATGACCCAGTGCTAGGGGAAGACTATTACAGTGTGGAAAATCCT
GCAAACAAAAGAAGGAGTACCCTCATCACAGTGCTT    837

AATATATCGGAAATTGAAAGTAGATTTTATAAACATCCATTTACCTGTTTTGCCAAGAATACACATGGT
ATAGATGCAGCATATATCCAGTTAATATATCCAGTC    942

ACTAATTTCCAGAAGCACATGATTGGTATATGTGTCACGTTGACAGTCATAATTGTGTGTTCTGTTTTC
ATCTATAAAATCTTCAAGATTGACATTGTGCTTTGG    1047

TACAGGGATTCCTGCTATGATTTTCTCCCAATAAAAGCTTCAGATGGAAAGACCTATGACGCATATATA
CTGTATCCAAAGACTGTTGGGGAAGGGTCTACCTCT    1152

Figure I (cont'd)

GACTGTGATATTTTTGTGTTTAAAGTCTTGCCTGAGGTCTTGGAAAAACAGTGTGGATATAAGCTGTTC
ATTTATGGAAGGGATGACTACGTTGGGGAAGACATT        1257

GTTGAGGTCATTAATGAAAACGTAAAGAAAAGCAGAAGACTGATTATCATTTTAGTCAGAGAAACATCA
GGCTTCAGCTGGCTGGGTGGTTCATCTGAAGAGCAA        1362

ATAGCCATGTATAATGCTCTTGTTCAGGATGGAATTAAAGTTGTCCTGCTTGAGCTGGAGAAAATCCAA
GACTATGAGAAAATGCCAGAATCGATTAAATTCATT        1467

AAGCAGAAACATGGGGCTATCCGCTGGTCAGGGGACTTTACACAGGGACCACAGTCTGCAAAGACAAGG
TTCTGGAAGAATGTCAGGTACCACATGCCAGTCCAG        1572

CGACGGTCACCTTCATCTAAACACCAGTTACTGTC―――――ACCAGCCACTAAGGAGAAAC
TGCAAAGAGAGGCTCACGTGCCTCTCGGGTAGCATGGA        1665

GAAGTTGCCAAGAGTTCTTTAGGTGCCTCCTGTCTTATGGCGTTGCAGGCCAGGTTATGCCTCATGCTG
ACTTGCAGAGTTCATGGAATGTAACTATATCATCCT        1770

TTATCCCTGAGGTCACCTGGAATCAGATTATTAAGGGAATAAGCCATGACGTCAATAGCAGCCCAGGGC
ACTTCAGAGTAGAGGGCTTGGGAAGATCTTTTAAAA        1875

INTERLEUKIN RECEPTOR EXPRESSION INHIBITING ANTISENSE OLIGONUCLEOTIDES

FIELD OF THE INVENTION

This invention relates to novel compounds that block expression of interleukin receptors thereby blocking the physiologic effects of interleukin.

BACKGROUND OF THE INVENTION

The cytokines interleukins 1 alpha and 1 beta (collectively IL-1) play a central role in mediating immune responses and inflammatory reactions. These cytokines have been implicated in several inflammatory diseases including rheumatoid arthritis. Thus, much pharmaceutical research has been directed toward discovery of chemicals that influence physiologic effects of IL-1 either by affecting IL-1 levels or interacting with IL-1 receptors.

IL-1 receptors are specific protein molecules present on the surface of cells responsive to IL-1. IL-1 exerts its effects by binding to these receptor molecules. Molecular cloning experiments have shown the human T-cell IL-1 receptor to be a 557-amino acid transmembrane protein coded for by a DNA sequence of approximately 1900 nucleotides. Sims, J. E. et al: *Proc. Natl. Acad. Sci. U.S.A.* 86:8946-8950 (Nov. 1989). Similar experiments have shown the human fibroblast IL-1 receptor gene to have the same nucleotide sequence. Chua, A. O. and Gubler, U., *Nucleic Acid Res.* 17:10114 (1989).

The native DNA segment coding for IL-1 receptors, as all such mammalian DNA strands, has two strands; a sense strand and an antisense strand held together by hydrogen bonding. The messenger RNA coding for the receptors has the same nucleotide sequence as the sense strand except that the DNA thymidine is replaced by uridine. Thus, synthetic antisense nucleotide sequences should bind with the DNA and RNA coding for the receptors. Because the binding strength of the DNA sense and antisense strands is the total of the hydrogen bonds between the 1900 nucleotide base pairs, the binding of a short, i.e. less than 50 nucleotide, antisense sequence to the RNA coding for the IL-1 receptor would be expected to be relatively weak.

Synthetic antisense polynucleotide sequences have been shown to reversibly reduce expression of Torpedo acetylcholine receptors in cultured Xenopus oocytes. Sumikawa, K. and R. Miledi, *Proc. Natl. Acad. Sci. U.S.A.* 85: 1302-1306 February 1988). Antisense polynucleotide sequences also have been shown to inhibit expression of T-cell receptor expression in T-cell hybridomas. Zhenc, H. et al, *Proc. Natl. Acad. Sci. U.S.A.* 86: 3758-3762 (May 1989). Synthetic polynucleotides in which the phosphate group is replaced by a phosphorothioate or methylphosphonate generally have been proposed as possible pharmaceutical agents. Cohen, J. S., *Trends in Pharmacol Sciences:* 10(11) 435-437 November 1989).

Therefore, synthetic modified polynucleotide sequences that block expression of receptors when administered internally are needed to allow use of antisense strands as therapeutic agents. Specifically needed are polynucleotide sequences which when administered safely and effectively block expression of IL-1 receptors.

SUMMARY OF THE INVENTION

The invention resides in the discovery that IL-1 receptor expression can be inhibited in humans by administration of oligonucleotide compounds of Formula I: I:

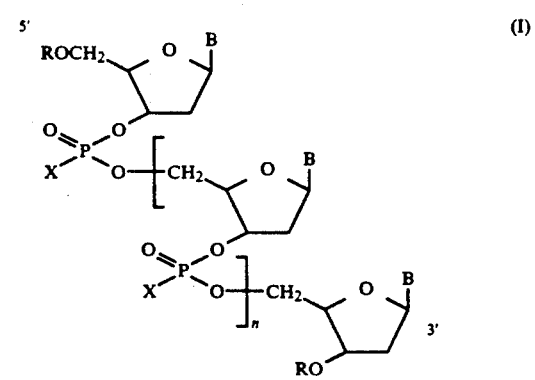

in which

X each independently is O, S, or $C_{1-4}$ alkyl provided at least about 4% are S or $C_{1-4}$ alkyl;

B each is Ade, Gua, Cyt, or Thy selected such that the oligonucleotide binds to the sense DNA strand coding for human IL-1 receptors thereby inhibiting expression thereof;

R each independently is H or $C_{1-4}$ alkyl or P(O)(O)-substituted acridine; and n is 12 to 30; or pharmaceutically acceptable salts or hydrates thereof.

A suitable subgeneric group of compounds are Formula I compounds excluding those in which R is P(O)(O)-substituted acridine.

Formula I compounds optionally may include intercalating molecules or ribozyme sequences.

Formula I includes compounds which have intervening sequences of other nucleotides or non-nucleotide molecules provided such compounds bind IL-1 receptor DNA and inhibit its expression.

The invention also is a method for inhibiting IL-1 receptor expression in humans that comprises administering internally to a subject an effective amount of a Formula I compound.

The invention includes pharmaceutical compositions comprising Formula I compounds and a pharmaceutically acceptable carrier.

BRIEF DESCRIPTION OF THE DRAWING

FIG. 1 is the sense strand of the DNA sequence coding for human IL-1 receptors as determined by Sims, et al; *Proc. Natl. Acad. Sci.* U.S.A. 86:8946-8950 November 1989).

DETAILED DESCRIPTION OF THE INVENTION

The oligonucleotide compounds of the invention bind to the messenger RNA coding for human IL-1 receptors thereby inhibiting expression of these receptors. Preferred compounds of the invention are antisense to the DNA sequence coding for human IL-1 receptors shown in FIG. 1.

In FIG. 1 and in the specification and claims, the letters A,G, C, T, and U respectively indicate nucleotides in which the nucleoside is Adeniosine (Ade), Guanosine (Gua), Cytidine (Cyt), Thymidine (Thy), and Uracil (Ura). As used in the specification and claims compounds that are antisense to the IL-1 receptor DNA sense strand are compounds which have a nucleoside sequence complementary to the sense strand. Table 1 shows the four possible sense strand nucleosides and their complements present in an antisense compound.

TABLE 1

| Sense | Antisense |
|---|---|
| Ade | Thy |
| Gua | Cyt |
| Cyt | Gua |
| Thy | Ade |

The compounds of Formula I also differ from native DNA in that some or all of the phosphates in the nucleotides are replaced by phosphorothioates (R=S) or methylphosphonates(R=CH3) or other $C_{1-4}$ alkylphosphonates. The compounds of Formula I optionally may be further differentiated from native DNA by replacing one or both of the free hydroxy groups of the sense molecule with $C_{1-4}$ alkoxy groups (R=$C_{1-4}$ alkoxy). As used herein $C_{1-4}$ alkyl means a branched or unbranched hydrocarbon having 1 to 4 carbon atoms.

Formula I compounds also may be substituted at the 3' and/or 5' ends by a substituted acridine derivative. As used herein "substituted acridine" means any acridine derivative capable of intercalating nucleotide strands such as DNA. preferred substituted acridines are 2-methoxy-6-chloro-9-pentylaminoacridine, N-(6-chloro-2-methoxyacridinyl)-O-methoxydiisopropylaminophosphinyl-3-aminopropanol, and N-(6-chloro-2-methoxyacridinyl)-O-methoxydiisopropylaminophosphinyl-5-aminopentanol. Other suitable acridine derivatives are readily apparent to persons skilled in the art. Additionally, as used herein "P(0)(0)-substituted acridine" means a phosphate covalently linked to a substituted acridine.

Formula I compounds also may include ribozyme sequences inserted into their nucleotide sequence. The ribozyme sequences are inserted into Formula I compounds such that they are immediately preceded by AUC, UUC, GUA, GUU, GUC, or, preferably, CUC. The ribozyme sequence is any sequence which can be inserted and causes self-cleavage of messenger RNA. The sequence CUG AUG AGU CCG UGA CGA A is preferred. Other such sequences can be prepared as described by Haseloff and Gerlach. Nature (Aug. 18, 1988) 334: 585-591.

The compounds of Formula I have about 12 to 30 nucleotides. As used herein, the term "nucleotides" includes nucleotides in which the phosphate moiety is replaced by phosphorothioate or alkylphosphonate and the nucleotides may be substituted by substituted acridines. Preferred Formula I compounds have 13 to 22 nucleotides. More preferred are compounds having 16 to 20 nucleotides. Most preferred are compounds having 18 nucleotides. Compounds having fewer than 12 nucleotides are less desirable because they generally have less specificity and compounds having greater than 30 nucleotides are less desirable because they generally are not sufficiently soluble in aqueous media and thus are less likely to enter cells.

Although Formula I compounds that are antisense to human IL-1 receptor DNA are preferred, Formula I includes nucleotide compounds which lack a complement for each nucleotide in a segment of the DNA sense strand provided such compounds have sufficient binding affinity for human IL-1 receptor DNA to inhibit receptor expression. The procedures of Example (3) are useful to determine whether specific oligonucleotides are effective in inhibiting IL-1 receptor expression.

Formula I compounds in which R is H are preferred. R, however, can be $C_{1-4}$ alkyl provided the resulting compounds retains sufficient binding affinity for the IL-1 DNA sense strand to inhibit expression of IL-1 receptors.

Formula I compounds in which one or more X is S are prepared by published procedures which are incorporated herein by reference. Stec, W. J. et al, J. Am. Chem. soc. (1984) 106: 6077-6079; Adams, S. P. et al; J. Am. Chem. Soc. (1983) 105: 661; Caruthers, M. H., et al; Genetic Engineering, Settlow, J. Hollander. A. Eds; Plenum Press: New York (1982) 4:1; Broido, M. S. et al; Biochem Biophys. Res. Commun. (1984) 119:663. The reaction scheme described in these published procedures is shown is Scheme I, below. This reaction scheme is conducted on a solid support.

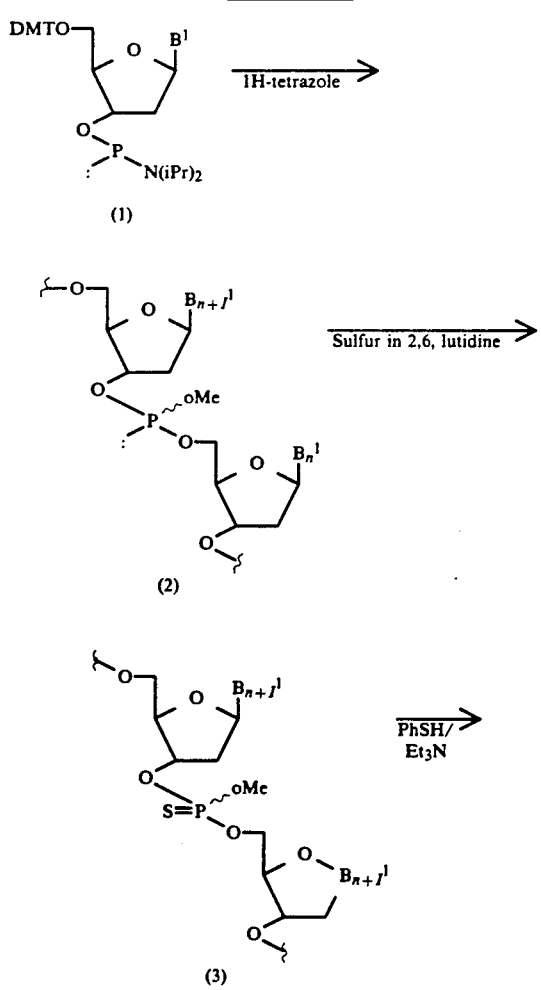

-continued
SCHEME I

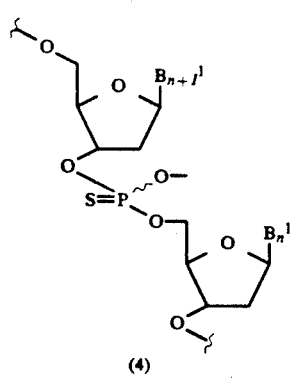

B¹ is N-benzoyl adenine, N-isobutrylguanine,
N-benzoylcytosine, or thymine

Scheme I shows 1H-tetrazole-catalyzed coupling of phosphoramidites (1) to give phosphate intermediates (2) which are reacted with sulfur in 2,6-lutidine to give phosphate compounds (3). Compounds (4) are prepared by treating compounds with thiophenoxide (1:2.2 thiophenol/triethylamine/tetrahydrofuran, room temperature, 1 hour). The reaction sequence is repeated until an oligonucleotide of the desired length has been prepared. Compounds (4) then are cleaved from the support by treating with ammonium hydroxide at room temperature for 1 hour. Compounds (4) then are further deprotected by heating at about 50° C. overnight to yield Formula I compounds.

Formula I compounds in which at least one X is oxygen are prepared by substituting $I_2$-$H_2O$ for sulfur in 2,6-lutidine in Scheme I.

Formula I compounds in which at least on X is $CH_3$ or other $C_{1-4}$ alkyl are prepared by published procedures that are incorporated herein by reference. Aqarwal, K. L. and Riftina, F., *Nucl. Acids Res* (1979) 6: 3009-3023; The reaction scheme described in this reference is shown in Scheme II, below. The Scheme II reaction sequence is conducted on a solid support.

SCHEME II

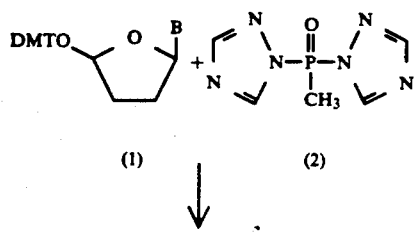

-continued
SCHEME II

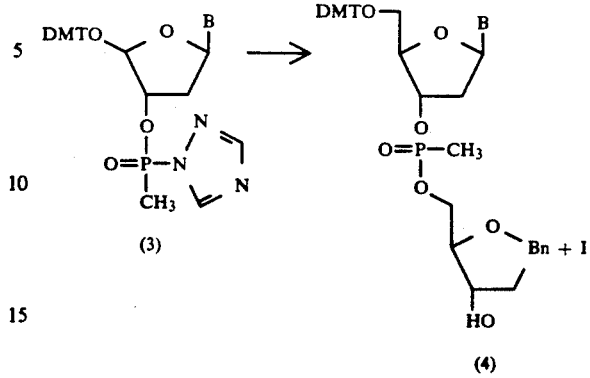

Scheme II shows phosphorylation of the 3'-hydroxyl group of a 5'-protected nucleoside (1) using methyl-phosphonoditriazolide (2) as the phosphorylating reagent followed by benzene sulfonyl-catalyzed coupling of the methylphosphonates (3) to yield compounds (4). Compounds (2) are prepared in situ from equimolar quantities of methylphosphonodichloridate, triethylamine, and triazole. Benzene sulfonyl tetrazole also was prepared in situ from pyridine, benzene-sulfonci acid and triethylamine.

Repeating this reaction sequence followed by cleavage from the support and deprotection yield Formula I compounds.

Formula I compounds in which R is $C_{1-4}$ alkyl are prepared by replacing the DMT-protected compounds with $C_{1-4}$ alkylethers in Schemes I and II.

Formula I compounds in which R is P(0)(0)-substituted acridine also are prepared by published procedures which are incorporated herein by reference. Asseline, U. and N. T. Thuong, *Tet. Letters* (1989) 30 (19): 2521-2524; Stein, C. A., et al., *Gene* (1988) 72: 333-341. These published procedures include synthesis of a nucleoside phosphoramidite-bearing acridine derivative which then is reacted with 2, 2'-dithiodiethanol attached to a support. The elongation chain then is carried out on an automatic solid-phase DNA synthesized as described above. These published procedures also include synthesis of nucleoside phosphoramidite-bearing acridine derivatives by reacting substituted 9-(3-hydroxypropyl) amino acridines with N-ethyldiisopropylamine followed by N,N-dissopropylmethylphosphonamidic chloride. Using an automated DNA synthesizer, Formula I compounds in which R is P (0)(0)-substituted acridine are prepared by an extra round of synthesis using the acridinyl phosphoramidites in acetomtrile.

Utility of formula (I) compounds in inhibiting expression of IL-1 receptors was demonstrated in vitro by the procedures of Example 3. The results of the Example 3 assay also show that compounds antisense to mouse IL-1 receptor DNA added to cultured mouse cells known to have IL-1 receptors and tumor necrosis factor receptors inhibited response to interleukin but did not affect response to tumor necrosis factor.

The compounds of Formula I can be incorporated into convenient pharmaceutical dosage forms such as capsules, tablets, or injectable preparations. Solid or liquid pharmaceutical carriers can be employed. Solid carriers include starch, lacrose, calcium sulfate dehydrate, terra alba, sucrose, tale, gelatin, agar, pectin, acacia, magnesium stearate, and stearic acid. Liquid carriers include syrup, peanut oil, olive oil, saline, water, and liposomal preparations. Similarly, the carrier or diluent may include any prolonged release material, such as glyceryl monostearate of glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule., sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula I in a pharmaceutical dosage unit as described above will be an efficacious, nontoxic quantity selected from the range of 0.1-100 mg/kg of active compound, preferably 0.1-50 mg/kg. The selected dose is administered to a human patient in need of inhibition of IL-1 receptor expression from 1-6 or more times daily, orally, rectally, by injection, or continuously by infusion. Oral dosage units for human administration, generally uses lower doses.

The following examples are illustrative of Formula (I) compounds and their preparation. The examples are not intended to limit the scope of the invention as defined above and claimed below.

EXAMPLE 1

5'-TCT GAG TAA CAC TTT CAT-3'
(Phosphorothioate)

The above oligonucleotide was synthesized using an automated polynucleotide synthesizer following the procedure described in Scheme I, above.

EXAMPLE 2

5'TCT GAG TAC UGA UGA GUC CGU GAG GAG GAA ACA CTT TCAT-3' (Phosphorothrioate)

The above oligonucleotide is a compound including a ribozyme sequence (underlined). This compound was prepared as described in Example 1.

EXAMPLE 3

In Vitro and In Vivo Effects of Oligonucleotides

1. IL-1 stimulated prostaglandin $E_2$ synthesis.

Effects of expression of IL-1 receptors by murine and human fibroblasts were assessed as follows Murine Swiss 3T3 cells (American Type Culture Collection ATCC CCL 92) or human dermal fibroblasts (primary culture) were grown in 96-well plates in Dulbecco's modified Eagles medium containing either 10% calf serum or 10% fetal bovine serum, respectively (Grand Island Biological Company), to confluency. The culture medium was replaced with identical medium except that the serum had been heat-inactivated at 65° C. for 15 minutes to inactivate nucleases. Oligonucleotides (30 $\mu$m) were added to the cultures and incubated for 48 hours. IL-1$\beta$ (10 $\mu$/ml) was then added for 6 hours and medium was collected for quantitation of prostaglandin $E_2$ by radioimmunoassay (Burch and Axelrod, Proc Nat'l Acad. Sci. USA 84:6374,1987). Oligonucleotides (phosphorothioates) S0-1, S0-2 and S0-3 are antisense to murine IL-1 receptor DNA and S0-6 is antisense to human IL-1 receptor DNA.

TABLE 1

| Treatment | $PGE_{2, pg/well}$ |
|---|---|
| Swiss 3T3 cells | |
| Control | 60 |
| IL-1 | 375 |
| +S0-1 | 125 |
| +S0-2 | 285 |
| +S0-3 | 330 |
| +S0-6 | 330 |
| Human cells | |
| Control | 25 |
| IL-1 | 285 |
| +S0-1 | 275 |
| +S0-6 | 180 |

The data demonstrates that sequences derived from the murine IL-1 receptor (S0-1, S0-2, S0-3) inhibit responses to IL-1 in murine (3T3) cells while human sequences (S0-6) do not, and vice versa.

2. IL-1 receptor expression

Swiss 3T3 fibroblasts were cultured exactly as described in 1. Oligonucleotide mS0-1 (mouse) 30 $\mu$M, was added and cultures were incubated for 48 hours. Then media were removed and replaced with ice-cold Hawk's balanced salt solution containing ($^{125}$I)-IL-1 (New England Nuclear) plus various concentrations of unlabeled IL-1 (Boehringer Mannheim). Cultures were incubated in ice baths for 60 minutes. Then media were aspirated and washed four times with ice-cold Hanks balanced salt solution. Cells were solubilized by incubation with 0.1% sodium dodecyl sulfate in water, then radioactivity was quantitated. Scatchard analysis was carried out using LIGAND (Munson and Rodbard). Anal. Biochem. 107,220 (1980).

TABLE 2

| Condition | $K_D$ | Bmax |
|---|---|---|
| Control | 41 pM | 2.05 pM |
| mS0-1, 30 $\mu$M | 38 pM | 0.85 pM |

These data show that the oligonucleotide reduced the number of IL-1 receptors without affecting binding affinity.

3. IL-1 stimulated nertrophil accumulation in vivo.

Hair was removed from the backs of CF-1 mice. Six spots were marked on the backs with indelible ink. Two spots were used as control, two were injected with 100 $\mu$l of 0.9% saline, two with 100 $\mu$l S0-6 (3 nmol), and two with 100 $\mu$l S0-1 (3 nmol). Injections were repeated every 24 hours into the same spots as appropriate. At 18 hours prior to scheduled sacrifice animals were injected i.p. with 10 $\mu$Ci [$^3$H] thymidine to label neutrophils. Four hours prior to sacrifice appropriate spots were injected with 10,000 $\mu$IL-1 alpha (Boehringer Mannheim). Animals were sacrificed by cervical dislocation at 24, 48, or 72 hours after the first injection with oligonucleotide i.e. after 1, 2, or 3 injections. Skin punches, 7 mm in diameter, were taken with injection sites at the centers. The skin samples were digested in Redisolve® (Beckman) then counted using liquid scintillation spectrometry. Background radioactivity in non-IL-1 injected spots was subtracted from each measurement.

These data demonstrate that mouse IL-1 receptor antisense oligonucleotides reduce IL-1 stimulated neutrophil accumulation in mice and human IL-1 receptor antisense oligonucleotides do not.

TABLE 3

| Condition | SO-6 | SO-1 |
|---|---|---|
| 24 hr. | 676 ± 788 | 6910 ± 903 |
| 48 hr. | 5509 ± 548 | 4504 ± 299 |
| 72 hr. | 5867 ± 706 | 2513 ± 508 |

EXAMPLE 4

Liposome Formulation and Evaluation

Liposomes were prepared by dissolving 5 mg phosphatidylserine in chloroform, then vaporizing to a film under $N_2$ using a rotary evaporator. The lipid was resuspended in 0.2 ml EDTA buffer with rigorous vortexing to form vesicles. Calcium was added in excess to form cochleate bodies. The oligonucleotides were then added and the mixtures were incubated for 1 hour. EDTA then was added and the pH adjusted to 7. The preparation was centrifuged at 100,000×g for 30 minutes to collect the liposomes and the pellet was rinsed three times in phosphate buffered saline.

For the experiment human dermal fibroblasts were incubated for 18 hours with IL-1, 100 u/ml., to down-regulate existing receptors. The cells were then rinsed three times with phosphate-buffered saline containing 2 mM calcium and 0.1 mM magnesium to remove IL-1, then incubated 30 minutes. Liposomes were then added and the mixture was incubated for 30 minutes. Finally, polyethylene glycol (M.W.6000) was added for 1 minute, then the cultures were rinsed three times in culture medium. Cultures were incubated for eight hours, then stimulated with IL-1, 10 U/ml for 4 hours. Media were collected for radioimmunoassy of $PGE_2$.

TABLE 4

| Treatment | $PGE_2$, pg/well |
|---|---|
| Control (empty liposome) | 65 |
| IL-1 (empty liposome) | 398 |
| +SO-6 (30 μM) | 74 |

Thus, liposomes deliver SO-6 to cultured cells.

EXAMPLE 5

A pharmaceutical composition of a Formula I compound is prepared by dispersing 10 mg of the Example 1 compound in normal saline followed by sterilization to yield a composition suitable for injection.

While the preferred embodiments of the invention are illustrated by the above, it is to be understood that the invention is not limited to the instructions contained herein and that the right to all modifications coming within the scope of the following claims is reserved.

Presently contemplated equivalents of the invention are oligonucleotide compounds having a structure similar to those of Formula I, such as alkyl homologs, which are effective in reducing expression of human IL-1 receptors. Other equivalents include Formula I compounds having additional nucleotides interlineated in the nucleotide sequence of Formula I compounds provided such compounds retain efficacy in inhibiting IL-1 receptor expression.

What is claimed is:

1. A compound represented by the formula:

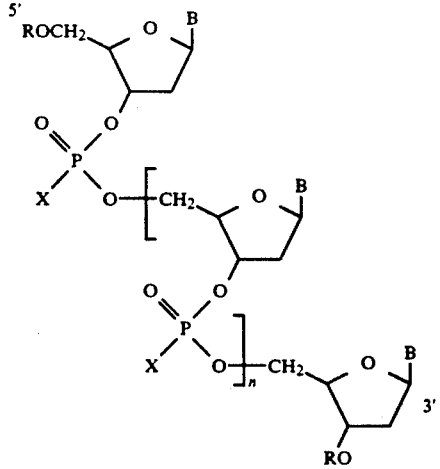

in which

X each independently is O, S, or $C_{1-4}$ alkyl provided at least about 4% are S or $C_{1-4}$ alkyl;

B each is Ade, Gua, Cyt, or Thy selected such that the oligonucleotide binds to the sense DNA strand coding for human IL-1 receptors thereby inhibiting expression thereof;

R each independently is H or $C_{1-4}$ alkyl or P(O)(O)-substituted acridine wherein the substituted acridine is 2-methoxy-6-chloro-9-pentylamino acridine, N-(6-chloro-2-methoxyacridinyl)-O-methoxydiisopropylaminophosphinyl-3-aminopropanol, or N-(6-chloro-2-methoxyacridinyl)-O-methoxydiisopropylaminophosphinyl-5-aminopentanol; and n is 12 to 30; or pharmaceutically acceptable salts or hydrates thereof.

2. A compound of claim 1 in which B is selected such that the compound is antisense to the sense strand coding for human IL-1 receptors.

3. A compound of claim 2 in which B is 5'-TCTGAGTAACACTTTCAT-3' and X is S.

4. A pharmaceutical composition useful for inhibiting IL-1 receptor expression comprising a pharmaceutical carrier and a compound of claim 1.

5. A pharmaceutical composition of claim 4 in which B is selected such that the compound is antisense to the sense strand coding for human IL-1 receptor DNA.

6. A pharmaceutical composition of claim 5 wherein the pharmaceutical carrier is a liposome formulation.

7. A pharmaceutical composition of claim 5 in which B is TCTGAGTAACACTTTCAT-3', X is S, and R is H.

8. A method for inhibiting expression of IL-1 receptors in a human in need thereof that comprises administering to a subject an effective amount of a compound represented by the formula:

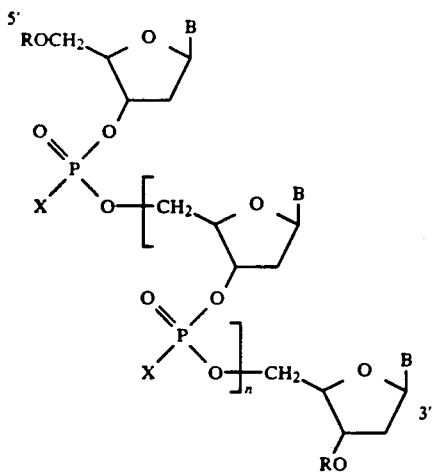

in which

X each independently is O, S, or $C_{1-4}$ alkyl provided at least about 4% are S or $C_{1-4}$ alkyl;

B each is Ade, Gua, Cyt, or Thy selected such that the oligonucleotide binds to the sense DNA strand coding for human IL-1 receptors thereby inhibiting expression thereof;

R each independently is H or $C_{1-4}$ alkyl or P(O)(O)-substituted acridine wherein the substituted acridine is 2-methoxy-6-chloro-9-pentylamino acridine, N-(6-chloro-2-methoxyacridinyl)-O-methoxydiisopropylaminophosphinyl-3-aminopropanol, or N-(6-chloro-2-methoxyacridinyl)-O-methoxydiisopropylaminophosphinyl-5-aminopentanol; and n is 12 to 30; or pharmaceutically acceptable salts or hydrates thereof.

9. A method of claim 8 in which B is selected such that the compound is antisense to the DNA coding for human IL-1 receptors.

10. A method of claim 8 in which B is 5' TCTGAG-TAA CACTTTCAT-3', X is S, and R is H.

* * * * *